United States Patent [19]
Mochizuki et al.

[11] Patent Number: 5,725,849
[45] Date of Patent: Mar. 10, 1998

[54] A COMMUNICATION DISRUPTANT FOR CONTROLLING *PANDEMIS HEPARANA*

[75] Inventors: Fumiaki Mochizuki, Niigata; Makoto Minamishima, Nagano, both of Japan

[73] Assignees: Nagano Prefecture, Nagano; Shin-Etsu Chemical Co., Ltd., Tokyo, both of Japan

[21] Appl. No.: 607,938

[22] Filed: Feb. 28, 1996

[30] Foreign Application Priority Data

Mar. 1, 1995 [JP] Japan .................................. 7-41987

[51] Int. Cl.$^6$ .............................. A01N 37/06; A01N 31/02
[52] U.S. Cl. ............................... 424/84; 514/546; 514/739
[58] Field of Search .............................. 424/84; 514/546, 514/739

[56] References Cited

U.S. PATENT DOCUMENTS 3,980,771  9/1976  Meijer et al. .............................. 424/84

FOREIGN PATENT DOCUMENTS 2933749  3/1981  Germany .

OTHER PUBLICATIONS

Tamaki, Y. et al (1975) Inhibition of the sexual behavior of the smaller tea tortrix moth by the sex pheromone and its components (Jap. J. Appl. Entomol. Zool. 19: 187–192.

Frerot B. et al. (1982) Sex pheromone of Pandemis heparana, J. Chem. Eco. 8: 663–670.

Ohira, Y. and T. Oku (1992) Selective control of the apple tortrix means of mating disruption and an egg parasite: a preliminary account. Acta Phytopathologia et Entomologica Hungarica 27 (1–4), 501–506.

Gut, L.J. and J. F. Brunner (1992) Mating disruption as a control for codling moth and leafrollers. Good Fruit Grower 56–60.

Sugue, H. et al (1992) Sex pheromone of *Pandemis heparana*. Annual Report in National Institute of Agro–Environmental Science.

Sugue, H. et al (1993) Sex pheromone of *Pandemis heparana*. Annual Report in National Institute of Agro–Environmental Science.

Brighton Crop Protection Conference–Pests and Diseases. No. 3, 1992, pp. 1193–1198, P. Van Deventer, et al.

Proc. Exerp. & Appl. Entomol., vol. 4, pp. 109–114 J.N.C. Van der Pers & A. K. Minks.

Chemical Abstracts 103: 2089e, 1985.

Chemical Abstracts 102: 162155f, 1985.

Chemical Abstracts 105: 220935k, 1986.

Primary Examiner—John Pak
Attorney, Agent, or Firm—McAulay Fisher Nissen Goldberg & Kiel, LLP

[57] ABSTRACT

Herein disclosed are a communication disruptant for controlling *Pandemis heparana* which is a leaf roller of an apple pest in the world. The communication disruptant comprises (Z)-11-tetradecenyl acetate as active ingredient, and a content of its geometrical isomer, (E)-11-tetradecenyl acetate, should be not more than 1% on the basis of the weight of the active ingredient. Because the present invention indicates that (E)-11-tetradecenyl acetate is an inhibitor of communication disruption effect of the active ingredient. Moreover, the present invention also indicates that (Z)-11-tetradecenol show synergistic effect to the active ingredient, when the alcohol content is not more than 5% on the basis of the weight of the active ingredient.

4 Claims, No Drawings

A COMMUNICATION DISRUPTANT FOR CONTROLLING *PANDEMIS HEPARANA*

BACKGROUND OF THE INVENTION

The present invention relates to a communication disruptant for controlling *Pandemis heparana*.

The control of a harmful insect through communication disruption is performed by diffusing a large amount of a communication disruptant at the habitat, in order to disturb the sexual communication to reduce the population of density of the next generation.

Four kinds of leaf rollers, *Adoxophyes sp.*, *Adoxophyes orana*, *Archips breviplicanus* and *Archips fuscocupreanus*, listed in Table 1 possess (Z)-11-tetradecenyl acetate (hereinafter also referred so as Z11-14:Ac ) and (E)-11-tetradecenyl acetate (hereinafter also referred to as E11-14:Ac) as components of their sex pheromones. The ratio of Z11-14:Ac and E11-14:Ac in the sex pheromone of each leaf roller is quite different. However it has been known that a mixture of Z11-14:Ac and several percent of E11-14:Ac is the best disruptant against the leaf rollers rather than their proper sex pheromone mixture. Moreover, it has also been known that the disruptant Z11-14:Ac with several percent of E11-14:Ac ensures a high communication disruption effect on *Homona magnanima*, although the leaf roller does not release E11-14:Ac as a component of the sex pheromone at all (Table 1).

TABLE 1

List Of sec pheromones and disruptants used for leaf rollers.

| Leaf Roller | | Attractant (Sex Pheromone) (ratio) | Communication Disruptant (ratio) | Contorol effect of the disruptant |
|---|---|---|---|---|
| Andoxophyes orna | tea | Z9–14:Ac(90) Z11–14:Ac(10) | Z11–14:Ac(100) E11–14:Ac(2–6) | good |
| Andoxophyes sp. | fruit | Z9–14:Ac(63) Z11–14:Ac(31) E11–14:Ac(4) 10Me-12:Ac(2) | Z11–14:Ac(100) E11–14:Ac(2–6) | good |
| Archips breviplicanus | fruit | Z11–14:Ac(30) E11–14:Ac(70) | Z11–14:Ac(100) E11–14:Ac(2–6) | good |
| Archips fuscoucu- preartus | fruit | Z11–14:Ac(80) E11–14:Ac(20) | Z11–14:Ac(100) E11–14:Ac(2–6) | excellent |
| Hamona magnamia | tea | Z11–14:Ac(88) Z9–12:Ac(9) 11–12:Ac(3) | Z11–14:Ac(100) E11–14:Ac(2–6) | good |
| Pandemis heparana | fruit | Z11–14:Ac(100) Z9–14:Ac(0.2) Z11–14:OH(21.6) | Z11–14:Ac(100) E11–14:Ac(2–6) | no good |

From the results, communication disruptant including a mixture of Z11-14:Ac and several percent of E11-14:Ac as active ingredients has been considered to have communication disruption effect against the leaf rollers which have Z11-14:Ac as a component in a sex pheromone gland. The communication disruptant including the mixture has already been put to practical use for controlling those five leap rollers. In fact, our investigation about the contents of E11-14:Ac based on the amount of Z11-14:Ac in commercially available communication disruptants for controlling leaf roller indicated that 2.1%, 2.6%, 3.0%, 4.5% and 6.2% were found in the A,B,C,D and E Company's products respectively. All of these commercially available communication disruptant to leaf rollers comprise E11-14:Ac in an amount ranging from 2.1 to 6.2% based on the amount of Z11-14:Ac.

*Pandemis heparana* is a leaf roller of apple pest in the world. Its damage has not been serious in the conventionally controlled fields, because its larva is sensitive to insecticides. However, recently, it has become serious in the orchard of the reduced insecticide spraying. Therefore, it should be a key pest in fields which are subjected to Integrated Pest Management (IPM). There has been desired for the development of an effective means for controlling *Pandemis heparana* through communication disruption.

The sex pheromone of *Pandemis heparana* was identified as a mixture of three compounds including Z11-14:Ac as a major component (Table 1). Therefore it had been considered that the commercially available communication disruptants including the mixture of Z11-14:Ac and E11-14:Ac as the active ingredient might be effective to its control. However, they did not work for controlling *Pandemis heparana*.

It has been considered that the longevity and migratory of *Pandemis heparana* were the reason why communication disruptants did not work for controlling this insect. And it has also believed that the ability of Z11-14:Ac to disrupt their sexual communication is not affected by the percentage of E11-14:Ac. Moreover, communication disruption effect of (Z)-11-tetradecenol (hereinafter also referred to as Z11-14:OH) has not been investigated, nevertheless the alcohol was found in an amount as much as 20% based on the amount of the Z11-14:Ac in sex pheromone gland of *Pandemis heparana*.

The present invention has been developed for solving the foregoing problems associated with the conventional techniques, and accordingly it is an object of the present invention to provide a communication disruptant for controlling *Pandemis heparana*.

SUMMARY OF THE INVENTION

The inventors of this invention have conducted various studies to control *Pandemis heparana* through a communication disruption, and indicated two important results. The first is that E11-14:Ac is an inhibitor of communication disruption effect of Z11-14:Ac. Consequently, Z11-14:Ac with high purity is necessary to control *Pandemis heparana* through the communication disruption. The second is that small amount of Z11-14:OH (not more than 5%) is synergist of communication disruption effect of A11-14:Ac, although the sex pheromone of *Pandemis heparana* comprises Z11-14:OH in an amount as much as 20% based on the weight of Z11-14:Ac.

The present invention is the communication disruptant for controlling *Pandemis heparana*. The characteristics of the communication disruptant are as listed below.

i) The active ingredient of the communication disruptant is Z11-14:Ac.

ii) The amount of geometrical isomer (E11-14:Ac) is not more than 1.0% based on the weight of Z11-14:Ac in the communication disruptant. It is to be desired that the rate of E11-14:Ac is not more than 0.5%.

iii) The amount of Z11-14:OH is not more than 5% based on the weight of Z11-14:Ac in the communication disruptant. It is to be desired that the rate of Z11-14:OH is from 0.1% to 2.0%.

The present invention will hereinafter be explained in more detail with reference to the following Examples, but the present invention is by no means limited to these specific Examples.

EXAMPLES 1 TO 4 AND COMPARATIVE EXAMPLES 1* TO 4* (TABLE 2)

Four types of communication disruptants were compared in the communication disruption effect and the control effect against *Pandemis heparana* in orchards. First type was a 100:0.3:0.3 mixture of Z11-14:Ac, E11-14:Ac, and Z11-14:OH (Examples 1 and 3). Second type was a 100:0.3 mixture of Z11-14:Ac and Z11-14:OH, and E11-14:Ac was eliminated from this at a level less than the detection limit by a gas-chromatogram (hereinafter also referred to as 0.0% of E11-14:Ac) (Examples 2 and 4). The high purity chemicals were obtained by purifying the conventional synthetic compounds using a silver nitrate-silica gel column. On the other hand, third and fourth types were commercially available disruptants and they were including 3.0% and 6.2% of E11-14:Ac, respectively (Comparative Examples 1* and 3*, and Comparative Examples 2* and 4*).

80 mg of the each disruptant was sealed in a polyethylene dispenser having an inner diameter of 0.8 mm and a length of 20 cm. 1,000 dispensers per hectare were applied uniformly in each test apple orchard (0.3 ha).

To estimate the communication-disruption effect of each disruptant, the mating ratio with tethered female method was measured in the center of each test orchard. Moreover, to estimate the control effect, numbers of young shoots damaged by larvae of *Pandemis heparana* (per 1,000 young shoots) were counted and rates of damaged young shoots were calculated in each test orchard.

EXAMPLES 5 TO 6 AND COMPARATIVE EXAMPLES 5* TO 7* (TABLE 3)

Two types of communication disruptants were prepared. First type was a 100:0.3 mixture of Z11-14:Ac and Z11-14:OH. E11-14:Ac in the type was eliminated at a level less than the detection limit by a gas-chromatogram (Examples 5 and 6). Second type was a 100:6.2:0.3 mixture of Z11-14:AC, E11-14:Ac, and Z11-14:OH (Comparative Examples 5* to 7*). 120 mg of the each disruptant was sealed in a polyethylene dispenser having an inner diameter of 0.8 mm and a length of 20 cm.

In this experiment, the communication disruption effect and control effect in various Concentration of each disruptant were examined in *Pandemis heparana*. In Example 5, the former type dispensers were applied in a rate of 1,000 dispensers per ha. In Example 6, the former type dispensers were applied in a rate of 500 dispensers per ha. In Comparative Example 5*, the later type dispensers were applied in a rate of 1,000 dispensers per ha. In Comparative Example 6*, the later type dispensers were applied in a rate of 2,000 dispensers per ha. In Comparative Example 7*, the later type dispensers were applied in a rate of 3,000 dispensers per ha. Each test apple orchard was 0.5 ha.

The above mentioned method were adopted to estimate the communication disruption and control effect in apple orchards.

TABLE 3

| Ex. No. | Rate of Component in Disruptant | | | Application dis./ha | Mating Ratio (%) | Rate of Damaged Young Shoots (%) |
|---|---|---|---|---|---|---|
| | Z11–14:Ac | E11–14:Ac | Z11–14:OH | | | |
| 5 | 100 | 0.0 | 0.3 | 1000 | 22.5 | 1.8 |
| 6 | 100 | 0.0 | 0.3 | 500 | 24.6 | 2.3 |
| 5* | 100 | 6.2 | 0.3 | 1000 | 80.0 | 26.3 |
| 6* | 100 | 6.2 | 0.3 | 2000 | 60.0 | 15.2 |
| 7* | 100 | 6.2 | 0.3 | 3000 | 60.0 | 16.7 |

*Comparative Example.

TABLE 2

| Ex. No. | Ratio of Component in Disruptant | | | Mating Ratio (%) | Rate of Damaged Young Shoots (%) |
|---|---|---|---|---|---|
| | Z11–14:Ac | E11–14:Ac | Z11–14:OH | | |
| 1 | 100 | 0.3 | 0.3 | 14.3 | 0.8 |
| 2 | 100 | 0.0 | 0.3 | 2.9 | 0.3 |
| 1* | 100 | 6.2 | 0.3 | 65.7 | 10.2 |
| 2* | 100 | 3.0 | 0.3 | 54.3 | 8.6 |
| 3 | 100 | 0.3 | 0.3 | 7.5 | 0.3 |
| 4 | 100 | 0.0 | 0.3 | 2.5 | 0.4 |
| 3* | 100 | 6.2 | 0.3 | 60.0 | 20.1 |
| 4* | 100 | 3.0 | 0.3 | 72.5 | 18.7 |

*Comparative Example.

The data listed in Table 2 clearly indicate that the communication disruptant of Examples 1 and 3 (0.3% of E11-14:Ac) and Examples 2 and 4 (0.0% of E11-14:Ac) can ensure excellent communication disruption effects and control effects against *Pandemis heparana* as compared with Comparative Examples 1 and 3 (6.2% of E11-14:Ac), and Comparative Examples 2 and 4.

The data listed in Table 3 clearly indicates that the dispenser including a 100:0.0:0.3 mixture of Z11-14:Ac, E11-14:Ac and Z11-14:OH shows excellent effect in reducing the mating ratio of and the rate of damage by *Pandemis heparana* (Examples 5 and 6), although the application was 500 dispensers per hectare. Moreover, the data also indicates that it is difficult to reduce the mating ratio and the damage by using the comparative dispenser comprising 6.2% of E11-14:Ac even if the application is increased to 2,000 or 3,000 dispensers per hectare (Comparative Examples 6* and 7*).

EXAMPLES 7 TO 10 AND COMPARATIVE EXAMPLES 8* TO 10* (TABLE 4)

Six kinds of communication disruptants listed in Table 4 were prepared by variously changing the content of E11-14:Ac in Z11-14:Ac containing Z11-14:OH for controlling *Pandemis heparana*. 80 mg of the each disruptant was sealed in a polyethylene dispenser having an inner diameter of 0.8 mm and a length of 20 cm. 1,000 dispensers per hectare were uniformly applied at a height of eye level in each test apple orchard. The above mentioned methods were adopted to estimate the communication disruption and control effect.

TABLE 4

| Ex. No. | Ratio of Component in Disruptant | | | Mating Ratio (%) | Rate of Damaged Young Shoots (%) |
| --- | --- | --- | --- | --- | --- |
| | Z11-14:Ac | E11-14:Ac | Z11-14:OH | | |
| 7 | 100 | 1.0 | 0.3 | 41.6 | 6.9 |
| 8 | 100 | 0.7 | 0.3 | 37.6 | 1.7 |
| 9 | 100 | 0.5 | 0.3 | 17.5 | 0.7 |
| 10 | 100 | 0.0 | 0.3 | 18.7 | 0.6 |
| 8* | 100 | 6.2 | 0.3 | 93.3 | 20.3 |
| 9* | 100 | 1.5 | 0.3 | 85.0 | 12.6 |
| 10* | (untreated orchard) | | | 96.6 | 39.6 |

*Comparative Example.

The data listed in Table 4 clearly indicates that the communication disruptants of Examples 7 to 10 show higher communication disruption effect and control effect than Comparative Examples 8* and 9* which have E11-14:Ac contents on the order of several percent based on the weight of Z11-14:Ac. Moreover, the disruptants including 0.0% and 0.5% of E11-14:Ac (Examples 10 and 9) show excellent effect in both communication disruption and control effect.

EXAMPLES 11 TO 15 AND COMPARATIVE EXAMPLES 11* TO 13* (TABLE 5)

Eight kinds of communication disruptants listed in Table 5 were prepared by variously changing the content of Z11-14:OH in Z11-14:Ac with 0.5% of E11-14:Ac for controlling *Pandemis heparana*. 80 mg of the each disruptant was sealed in a polyethylene dispenser having an inner diameter of 0.8 mm and a length of 20 cm. 1,000 dispensers per hectare were uniformly applied at a height of eye level in each test apple orchard. The above mentioned methods were adopted to estimate the communication disruption and control effect.

TABLE 5

| Ex. No. | Ratio of Component in Disruptant | | | Mating Ratio (%) | Rate of Damaged Young Shoots (%) |
| --- | --- | --- | --- | --- | --- |
| | Z11-14:Ac | E11-14:Ac | Z11-14:OH | | |
| 11 | 100 | 0.5 | 4.2 | 24.5 | 2.7 |
| 12 | 100 | 0.5 | 2.0 | 9.7 | 0.4 |
| 13 | 100 | 0.5 | 1.0 | 6.3 | 0.1 |
| 14 | 100 | 0.5 | 0.5 | 4.2 | 0.1 |
| 15 | 100 | 0.5 | 0.0 | 18.3 | 0.9 |
| 11* | 100 | 0.5 | 40.0 | 63.4 | 7.6 |
| 12* | 100 | 0.5 | 20.0 | 58.3 | 9.2 |
| 13* | 100 | 0.5 | 10.0 | 60.1 | 10.3 |

*Comparative Example.

The data listed in Table 5 clearly indicates that the communication disruptants of Examples 11 to 15 show higher communication disruption effect and control effect than Comparative Examples 11* and 13* which have more than 10.0% of Z11-14:OH based on the weight of Z11-14:Ac. Moreover, the disruptants including 0.5%, 1.0% and 2.0% of Z11-14:OH (Examples 12 to 14) show excellent effect in both communication disruption and control effect as compared with 4.2% and 0.0% of Z11-14:OH (Examples 11 and 15).

As has been explained above in detail, the present invention of the communication disruptant for controlling *Pandemis heparana* is quite different in the point of using Z11-14:Ac with geometric high purity from the conventional technique. Moreover, it is indicated that the communication and control effect of high purified Z11-14:Ac are improved by adjusting Z11-14:OH content to a level of not more than 5%. The present invention permits the prevention of damages by *Pandemis heparana* which has been considered difficult to control by anything beside insecticides. Accordingly, the present invention would be helpful in the development of highly safe cultivation.

What is claimed is:

1. A communication disruptant for controlling *Pandemis heparana* which comprises a combination of (Z)-11-tetradecenyl acetate, (Z)-11-tetradecenol and a contaminating amount of (E)-11-tetradecenyl acetate, wherein the amount of (Z)-11-tetradecenol is not more than 5% and the amount of (E)-11-tetradecenyl acetate is not more than 1% on the basis of the weight of the (Z)-11-tetradecenyl acetate.

2. The communication disruptant for *Pandemis heparana* of claim 1 wherein the amount of (E)-11-tetradecenyl acetate not more than 0.5%.

3. The communication disruptant for *Pandemis heparana* of claim 1, wherein the amount of (Z)-11-tetradecenol ranges from 0.1 to 2.0%.

4. The communication disruptant for *Pandemis heparana* of claim 2, wherein the amount of (Z)-11-tetradecenol ranges from 0.1 to 2.0%.

* * * * *